US006994861B2

(12) United States Patent
Brake et al.

(10) Patent No.: US 6,994,861 B2
(45) **Date of Patent: *Feb. 7, 2006**

(54) ATTENUATED LIVE *NEOSPORA* VACCINE

(75) Inventors: David A Brake, East Lyme, CT (US); Byron L Blagburn, Auburn, AL (US); David S Lindsay, Christiansburg, VA (US)

(73) Assignee: Pfizer Inc, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/669,941

(22) Filed: Sep. 24, 2003

(65) Prior Publication Data

US 2004/0062772 A1 Apr. 1, 2004

Related U.S. Application Data

(63) Continuation of application No. 09/952,388, filed on Sep. 12, 2001, now Pat. No. 6,656,479, which is a continuation of application No. 09/260,414, filed on Feb. 26, 1999, now abandoned, which is a continuation of application No. 08/967,744, filed on Nov. 10, 1997, now abandoned.

(60) Provisional application No. 60/031,248, filed on Nov. 12, 1996.

(51) Int. Cl.
*A61K 35/68* (2006.01)

(52) U.S. Cl. ............................... 424/265.1; 424/184.1; 424/269.1; 424/271.1; 435/243; 435/258.1; 435/69.1; 530/350

(58) Field of Classification Search ............... 424/93.1, 424/258.1, 271.1, 273.1, 190.1, 184.1, 274.1, 424/269.1, 191.1, 252.1, 200.1, 193.1, 265.1, 424/272, 234.1, 93.7, 93.2; 514/44; 435/6, 435/69.1, 258.1, 258.4, 476, 269.1, 254.2, 435/252.3, 320.1, 440, 7.92, 70.1, 4, 243; 536/23.7, 23.1; 530/350
See application file for complete search history.

(56) References Cited

U.S. PATENT DOCUMENTS

| | | | | |
|---|---|---|---|---|
| 5,643,718 | A | 7/1997 | Kim et al. | 435/6 |
| 5,707,617 | A * | 1/1998 | Conrad et al. | 424/93.1 |
| 5,889,166 | A | 3/1999 | Conrad et al. | 536/23.1 |
| 5,976,553 | A * | 11/1999 | Kim et al. | 424/271.1 |
| 6,071,737 | A | 6/2000 | Marsh et al. | 435/258.1 |
| 6,656,479 | B2 * | 12/2003 | Brake et al. | 424/269.1 |
| 6,716,423 | B1 * | 4/2004 | Conrad et al. | 424/93.1 |

FOREIGN PATENT DOCUMENTS

| | | |
|---|---|---|
| WO | 9717082 | 5/1997 |

OTHER PUBLICATIONS

Anderson, ML et al, Animal reproduction science, Jul. 2, 200, vol. 60-61, pates 417-431, Neosporosis in cattle, (abstrat only).*

Andrianarivo, AG et al, International journal of parasitology, Aug. 2000, vol. 30(9), pp. 985-990 (abstract only).*

Innes, EA et al, Trends in parasitology, Nov. 2002, vol. 18(11), pp. 497-504 (abstract only).*

Hemphill, A Infection and Immunity, vol. 64(10), pp. 4279-4287, Oct. 1996.*

Nishikawa, Y et al, Clinical and diagnostic laboratory immunology, vol. 8(4), pp. 811-817, Jul. 2001.*

Lindsay et al, American Journal of Vet. Res., vol. 56, pp. 1176-1180.*

Linday et al, Jan. 1996, American Journal of Vet. Res., vol. 57(1), pp. 68-72 (abstract only).*

Lindsay, DS et al, Journal of Parasitology, Feb. 1999, vol. 85(10, pp. 64-67 (abstract only).*

Lindsay et al (Sep. 1995), reference of record.*

Lindsay et al (Jan. 1996), reference of record.*

Hemphill et al (Oct. 1996), reference of record.*

Asbroek et al, 1990, Nature 348:174-175, "Targeted insertion of the neomycin phosphotransferase gene into the tubulin gene cluster of *Trypanosoma brucei*."

Barr et al., 1994, J. Vet. Diagn. Invest. 6:207-215, "Experimental reproduction of bovine fetal Neospora infection and death with a bovine Neospora isolate."

Cole et al., 1995, J. Parasitol. 81:730-732, "Vertical transmission of *Neospora caninum* in mice."

Conrad et al., 1993, Parasitol. 106:239-249, "In vitro isolation and characterization of a *Neospora* sp. from aborted bovine foetuses."

Cruz and Beverley, 1990, Nature 348:171-173, "Gene replacement in parasitic protozoa."

Donald and Roos, 1994, Mol. Biochem. Parasitol. 63:243-253, "Homologous recombination and gene replacement at the dihydrofolate reductase-thymidylate synthase locus in *Toxoplasma gondii*."

Dubey and Lindsay, 1993, Parasitol. Today 9:452-458 "Neosporosis."

Eid and Sollner-Webb, Proc. Natl. Acad. Sci. USA 88:2118-2121, "Stable integrative transformation of *Trypanosoma brucei* that occurs exclusively by homologous recombination."

(Continued)

*Primary Examiner*—Mark Navarro
*Assistant Examiner*—Ginny Allen Portner
(74) *Attorney, Agent, or Firm*—Thomas A. Wootton; Charles Ashbrook

(57) ABSTRACT

The present invention provides attenuated live cultures of the pathogenic protozoan parasite, *Neospora*, and live vaccines against neosporosis prepared therefrom which are useful in the prevention of clinical disease and abortion in mammals.

25 Claims, No Drawings

OTHER PUBLICATIONS

Kim et al., 1993, Science 262:911-914, "Gene replacement in *Toxoplasma gondii* with chloramphenicol acetyltransferase as selectable marker."

LeBowitz et al., 1990, Proc. Natl. Acad. Sci. USA 87:9736-9740, "Development of a stable Leishmania expression vector and application to the study of parasite surface antigen genes."

Gwo-Shu et al., 1990, Science 250:1583-1586, "Homologous recombination and stable transformation in the parasitic protozoan *Trypanosoma brucei*."

Lindsay et al., 1995, J. Parasitol. 81:313-315, "Mouse model for central nervous system *Neospora caninum* infections."

Lindsay et al., 1995, Am. J. Vet. Res. 56:1176-1180, "Abortions, fetal deaths, and stillbirths in pregnant pygmy goats inoculated with tachyzoites of *Neospora caninum*."

Lindsay and Dubey, 1989, J. Parasitol. 75:772-779, "*Neospora caninum* (Protozoa: Apicomplexa) infections in mice."

Lindsay and Dubey, 1989, J. Parasitol. 75:163-165, "In vitro development of *Neospora caninum* (Protozoa: Apicomplexa) from dogs."

Lindsay and Dubey, 1990, J. Parasitol. 76:410-413, "Infections in mice with tachyzoites and bradyzoites of *Neospora caninum* (Protozoa: Apicomplexa)."

Lindsay and Dubey, 1990, Can. J. Zool. 68:1595-1599, "*Neospora caninum* (Protozoa: Apicomplexa) infections in rats."

Lindsay et al., 1990, Infect. Immun. 58:2699-2700, "Infection of mice with *Neospora caninum* (Protozoa: Apicomplexa) does not protect against challenge with *Toxoplasma gondii*."

Marsh et al., 1995, J. Parasitol. 81:530-535, "Sequence analysis and comparison of ribosomal DNA from bovine *Neospora* to similar coccidial parasites."

Messina et al., 1995, Gene 165:213-217, "Stable DNA transformation of *Toxoplasma gondii* using phleomycin selection."

Sibley et al., 1994, Proc. Natl. Acad. Sci. USA 91:5508-5512, "Stable DNA transformation in the obligate intracellular parasite *Toxoplasma gondii* by complementation of tryptophan auxotrophy."

Soldati and Boothroyd, 1993, Science 260:349-352, "Transient transfection and expression in the obligate intracellular parasite *Toxoplasma gondii*."

Titus et al., 1995, Proc. Natl. Acad. Sci. USA 92:10267-10271, "Development of a safe live Leishmania vaccine line by gene replacement."

Adrianarivo et al, Intl. Journal of Parasitology 30:985-990.

Dreier et al., Intl. J. Parasitology 29:1627-1634.

Hemphill et al., 1996, Infect. Immun. 64(10):4279-4287.

Ho et al., 1996, J. Clin. Microbiol. 34(5):1203-1208.

Pfefferkorn and Pfefferkorn, 1976, Exper. Parasitol. 39:365-376, "*Toxoplasma gondii*: Isolation and Preliminary Characterization of Temperature-Sensitive Mutants."

Andrianarivo et al., International Journal of Parasitology, vol. 30, pp. 985-990, 2000.

Nishikawa, Y. et al., Clinical and diagnostic laboratory immunology, Jul. 2001, vol. 8(4), pp. 811-816 (abstract only).

Hemphill et al., Infection Immunity, vol. 64(10), pp. 4279-4287.

Lindsay, DS et al., American Journal of Veterinary Research, vol. 57(1), pp. 68-72, Jan. 1996, (abstract only).

* cited by examiner

ATTENUATED LIVE *NEOSPORA* VACCINE

CROSS REFERENCE TO RELATED APPLICATIONS

The present application is a continuation of application Ser. No. 09/952,388, filed Sep. 12, 2001 now U.S. Pat. No. 6,656,479, which is a continuation of application Ser. No. 09/260,414, filed Feb. 26, 1999, now abandoned, which is a continuation of application Ser. No. 08/967,744, filed Nov. 10, 1997, now abandoned, which claims priority from provisional application Ser. No. 60/031,248, filed Nov. 12, 1996.

FIELD OF THE INVENTION

The present invention relates to attenuated strains of the pathogenic protozoan, *Neospora*, and to live vaccines against neosporosis prepared from the attenuated strains which are useful in the prevention of clinical disease and abortion in mammals.

BACKGROUND OF THE INVENTION

*Neospora* is a pathogenic protozoan parasite of animals which has recently been recognized as a major cause of abortion, neonatal death, congenital infection, and encephalitic disease in mammals. Dubey and Lindsay, 1993, Parasitology Today, 9:452–458. *N. caninum* infects dogs, and congenitally infects pups, often leading to paralysis. Tachyzoites of *N. caninum* have been isolated from naturally infected pups. Lindsay and Dubey, 1989, J. Parasitol. 75:163–165. *Neospora* spp. are a major cause of abortion in dairy cattle. Cases of *Neospora*-related disease, i.e., neosporosis, have also been reported in goats, sheep and horses.

Although *N. caninum* is superficially similar to the pathogen, *Toxoplasma gondii, N. caninum* and *T. gondii* have been distinguished from each other antigenically and ultrastructurally. Dubey and Lindsay, 1993, above. In addition, *Neospora*-like protozoal parasites isolated from the brains of aborted bovine fetuses and continuously cultured in vitro were shown to be antigenically and ultrastructurally distinct from both *T. gondii* and *Hammondia hammondi*, and most similar to *N. caninum*. Conrad et al., 1993, Parasitology 106:239–249. Furthermore, analysis of nuclear small subunit ribosomal RNA genes revealed no nucleotide differences between *Neospora* spp. isolated from cattle and dogs, but showed consistent differences from *T. gondii*. Marsh et al., 1995, J. Parasitol. 81:530–535.

The etiologic role of a bovine isolate of *Neospora* in bovine abortion and congenital disease has been confirmed. Barr et al., 1994, J. Vet. Diag. Invest. 6:207–215. A rodent model of central nervous system neosporosis has been developed using inbred BALB/c mice infected with *N. caninum*. Lindsay et al., 1995, J. Parasitol. 81:313–315. In addition, models to study transplacental transmission of *N. caninum* in pregnant outbred and inbred mice have been described by Cole et al., 1995, J. Parasiol. 81:730–732, and by Long et al., 1996, J. Parasitol. 82:608–611, respectively. Furthermore, an experimental *N. caninum* pygmy goat model that closely resembles naturally acquired *Neospora*-induced cattle abortion has been demonstrated. Lindsay et al., 1995, Am. J. Vet. Res. 56:1176–1180.

WO 9525541 discloses a biologically pure culture of bovine *Neospora*, methods of detecting anti-*Neospora* antibodies and *Neospora*-specific nucleic acids, and a composition containing a bovine *Neospora* antigen and carrier for use as a vaccine. WO 9525541 does not, however, teach attenuated live cultures of *Neospora*, or live vaccines prepared therefrom which are able to trigger a protective immune response in a vaccinated animal.

SUMMARY OF THE INVENTION

In a first aspect, the present invention provides cultures of cells of a strain derived from a pathogenic parent strain of a species of *Neospora*, which cells exhibit attenuated pathogenicity compared to those of the parent strain but which are capable of triggering an immune response that protects a mammal against neosporosis when administered as a live vaccine.

In a second aspect, the present invention provides vaccines to protect a mammal against neosporosis, comprising an immunologically effective amount of live cells of a strain derived from a pathogenic parent strain of a species of *Neospora*, which cells exhibit attenuated pathogenicity compared to those of the parent strain but which are capable of triggering an immune response that protects the mammal against neosporosis when administered as a live vaccine, and a veterinarily acceptable carrier. Vaccines of the invention may further comprise one or more other components including, for example, an adjuvant. Vaccines of the present invention may be administered to any mammalian species susceptible to infection and disease caused by *Neospora* including, but not limited to, dogs, cows, goats, sheep and horses.

In a third aspect, the present invention provides methods for preparing cultures of attenuated cells from a pathogenic strain of *Neospora* for use in a vaccine that protects a mammal against neosporosis, comprising modifying cells from a pathogenic parent strain of a species of *Neospora*; selecting and clonally propagating one or more modified cells that exhibit attenuated pathogenicity compared to cells of the parent strain; and selecting and clonally propagating one or more attenuated cells which are capable of triggering an immune response that protects the mammal against neosporosis when administered in a live vaccine.

In a fourth aspect, the present invention provides methods for preparing a vaccine that protects a mammal against neosporosis, comprising modifying cells from a pathogenic parent strain of a species of *Neospora*; selecting and clonally propagating those modified cells that exhibit attenuated pathogenicity compared to cells of the parent strain but which are capable of triggering an immune response in the mammal that protects against neosporosis when administered in a live vaccine; and combining an immunologically effective amount of the attenuated cells with a veterinarily acceptable carrier in a form suitable for administration as a live vaccine to the mammal.

In a fifth aspect, the present invention provides methods for vaccinating a mammal against neosporosis, comprising administering to the mammal an immunologically effective amount of a vaccine comprising live cells of a strain derived from a pathogenic parent strain of a species of *Neospora*, which cells exhibit attenuated pathogenicity compared to those of the parent strain but which are capable of triggering an immune response that protects the mammal against neosporosis when administered as a live vaccine, and a veterinarily acceptable carrier.

In a sixth aspect, the present invention provides combination vaccines, comprising an immunologically effective amount of live cells of a strain derived from a pathogenic parent strain of a species of *Neospora*, which cells exhibit attenuated pathogenicity compared to those of the parent strain but which are capable of triggering an immune response that protects the mammal against neosporosis when administered as a live vaccine; one or more other antigens that trigger an immune response that protects the mammal against a disease or a pathological condition; and a veterinarily acceptable carrier. The combination vaccines may further comprise one or more other components including, for example, an adjuvant.

DETAILED DESCRIPTION OF THE INVENTION

Applicants have discovered that cells of a pathogenic strain of a species of *Neospora* may be attenuated, and that the resulting attenuated cells are capable of triggering an immune response that protects mammals against neosporosis when administer d as a live vaccine. The present invention thus provides cultures of cells of a strain derived from a pathogenic parent strain of a species of *Neospora*, which cells exhibit attenuated pathogenicity compared to those of the parent strain but which are capable of triggering an immune response that protects a mammal against neosporosis when administered as a live vaccine.

The present invention further provides methods for preparing cultures of attenuated cells of a species of *Neospora* for use in a vaccine that protects a mammal against neosporosis, comprising modifying cells from a pathogenic parent strain of a species of *Neospora*, for example, by high serial passage, or by exposure to a mutagenic agent, or by genetic engineering using recombinant DNA techniques; selecting and clonally propagating one or more modified cells that exhibit attenuated pathogenicity compared to cells of the parent strain; and selecting and clonally propagating one or more attenuated cells which are capable of triggering an immune response that protects the mammal against neosporosis when administered in a live vaccine.

As used herein, the term "neosporosis" refers to infection of a mammal by a species or strain of *Neospora*, or to any clinical symptom, condition, event or pathology associated with infection of the mammal by *Neospora*.

The term "attenuated" as used herein describes a cell, culture, or strain of *Neospora* exhibiting a detectable reduction in infectivity or virulence in vitro or in vivo as compared to that of the parent strain of *Neospora* from which the attenuated cell, culture, or strain is derived. Reduction in virulence encompasses any detectable decrease in any attribute of virulence, including infectivity in vitro or in vivo, or any decrease in the severity or rate of progression of any clinical symptom or condition associated with infection.

The term "parent strain" refers to a strain of *Neospora* which exhibits a relatively higher degree of pathogenicity when administered to a mammal than an attenuated strain which is derived therefrom by one or more passages in vivo or in vitro and/or one or more attenuation steps.

The present invention further encompasses preparation and use in a vaccine of cells of a strain of *Neospora* derived from a strain or species that is not pathogenic in a particular mammalian species, but which cells have been modified by chemical or genetic means to be capable of triggering a protective immune response in members of that mammalian species.

The live attenuated cells of the invention are capable of triggering an immune response that protects a mammal against neosporosis after one or more administrations as a live vaccine. A "protective immune response" is defined as any immunological response, either antibody or cell mediated immunity, or both, occurring in the mammal that either prevents or detectably reduces subsequent infection, or eliminates or detectably reduces the severity, or detectably slows the rate of progression, of one or more clinical symptoms or conditions associated with neosporosis. The term "immunologically effective amount" refers to that amount or dose of vaccine or antigen that triggers a protective immune response when administered to a mammal.

Preparation of Attenuated Strains of *Neospora*

Since the invention is based on the discovery that cells of a pathogenic strain of *Neospora* may be attenuated, and that the resulting attenuated cells are capable of triggering an immune response that protects a mammal against neosporosis when administered as a live vaccine, practice of the invention is not limited to any particular method of attenuation. Rather, attenuation of cells of a pathogenic strain of *Neospora* may be carried out by any techniques or procedures known in the art including, but not limited to, high serial passage, or exposure to a mutagenic agent, or by genetic engineering using recombinant DNA technology, or some combination thereof.

High serial passage may be carried out by repeated in vitro passaging of cells of a pathogenic strain of *Neospora* in susceptible host cells until sufficient attenuation occurs. Passaging may be conducted under specific environmental conditions to select for attenuated cells. For example, passaging, may be conducted at a temperature below that of the body temperature of the intended mammalian vaccinate to select for temperature-sensitive strains of *Neospora* that will not grow, or that will only grow at a reduced rate, when administered in a vaccine to the mammal.

Mutagenesis may be carried out by exposure of *Neospora* cells to either a chemical mutagen or to radiation, as described in the art. A non-limiting example of a chemical mutagen useful in the practice of the invention is N-methyl-N'-nitro-N-nitrosoguanidine (MNNG) (Sigma), the use of which is described below in Example 1. Radiation may be selected from either ultraviolet light or ionizing radiation.

The degree of exposure to the mutagen, i.e., the concentration of chemical mutagen, or the level of radiation, as well as the duration of exposure is preferably that amount which results in producing one or more viable cells of *Neospora* that exhibit an attenuated level of pathogenicity but that are capable of triggering an immune response that protects against neosporosis when administered as a live vaccine to a mammal. Appropriate parameters for use of mutagenic agents may be determined empirically using standard techniques.

Pathogenic strains of *Neospora* may also be attenuated using recombinant DNA technology according to techniques known in the art, and the present invention is intended to encompass such modified strains and vaccines prepared therefrom. Non-limiting examples of recombinant DNA techniques which may be used to practice the invention include gene replacement or gene knockout to disable one or more genes, resulting in a strain having an attenuated pathogenicity. Genes that may be disabled include, for example, an essential metabolic gene, or a gene encoding a virulence factor, or a gene encoding a surface antigen that plays a role in modulating the immune response in the mammalian host.

A non-limiting example of an essential metabolic gene that may usefully be targeted for disruption in the *Neospora* genome is the dihydrofolate reductase-thymidylate synthase (DHFR-TS) gene. Titus et al., 1995, Proc. Natl. Acad. Sci.

USA, 92:10267–10271, describe knocking out the DHFR-TS gene to produce a safe, live Leishmania vaccine, which publication is incorporated by reference. By disrupting the DHFR-TS gene in *Neospora*, auxotrophic mutants will be created that require thymidine for continued growth, that exhibit attenuated pathogenicity, and that are capable of triggering an immune response in a mammal that protects against neosporosis when administered as a live vaccine.

Recombinant DNA techniques for gene replacement or gene knockout are known in the art and include, but are not limited to, those that take advantage of homologous recombination. For example, cells of a pathogenic strain of *Neospora* may be transformed or transfected with a vector, such as a plasmid, comprising homologous nucleotide sequences that normally flank, or are located within, for example, an essential metabolic gene, preferably a single copy gene, in a pathogenic strain of *Neospora*. Between or within th homologous nucleotide sequences, the vector may further comprise a nucleotide sequence that corresponds to the nucleotide sequence in the pathogenic strain but which is defective as a result, for example, of a "non-silent" change or deletion in one or more nucleotides compared to the sequence from the pathogenic strain. Transformation of a cell of the pathogenic strain with the vector is followed by integration of the defective gene sequence into the *Neospora* genome, which also serves to replace the original or "wild-type" sequence. Thus, the targeted gene is disabled in the transformed cell. Transformed cells may then be screened for those cells that exhibit an attenuated pathogenicity. Transformed cells exhibiting attenuated pathogenicity may then be screened again for those cells that are capable of triggering an immune response in a mammal that protects against neosporosis when administered as a live vaccine.

To aid in the selection of transformants, the vector may be engineered to further comprise a coding sequence for a reporter gene product or other selectable marker. Reporter genes which may be useful in the invention are well-known in the art and include, for example, the gene encoding chloramphenicol acetyl transferase (CAT), or the gene encoding luciferase. A further non-limiting example of a reporter gene is a sequence encoding *E. coli* β-galactosidase, which can be inserted into the vector and used to confirm transformants by detecting enzymatic activity through conversion of a substrate such as, for example, red-β-D-galactopyranoside, to a colored product. Seeber and Boothroyd, 1996, Gene, 169:39–45, used this reporter enzyme to detect transformants in *Toxoplasma gondii*, which publication is incorporated herein by reference.

Coding sequences that encode selectable markers which may be useful in the invention are also wellknown in the art, and include those that encode gene products conferring resistance to antibiotics or anti-metabolites, or that supply an auxotrophic requirement. Examples of such sequences include those that confer resistance to hygromycin, or to neomycin, or to phleomycin. An example of the use of an antibiotic resistance marker in a different pathogen is presented by Messina et al., 1995, Gene, 165:213–217, which describes the use of a resistance marker for phleomycin to construct stable transformants in *T. gondii*, and which publication is incorporated herein by reference.

Any coding sequence for a reporter gene product or selectable marker should preferably be inserted into the vector in operative association with a regulatory element coding sequence. As used herein, a "regulatory element" includes, but is not limited to, inducible and non-inducible promoters, enhancers, operators and other elements known in the art that serve to drive and/or regulate expression. Also, as used herein, a DNA coding sequence is in "operative association" with one or more regulatory elements where the regulatory elements effectively regulate and allow for the transcription of the DNA coding sequence and/or the translation of the corresponding mRNA. For example, vectors for expression of the selectable marker ble in *Neospora* cells may be constructed by flanking the ble open reading frame (ORF) with regulatory regions from genes of *Neospora* or from the closely related Apicomplexa, *Toxoplasma*. The 5' flanking regions from different single copy *Neospora* or *Toxoplasma* genes may be used to express ble. Examples of single copy *Toxoplasma* genes are: (i) SAG1, encoding the major tachyzoite surface antigen, p30 (Burg et al., 1988, J. Immunol. 141:3584–3591); (ii) GRA1, encoding a secretory protein, p23 (Cesbron-Delauw et al., 1989, Proc. Natl. Acad. Sci. 86:7537–7541); and (iii) GRA2, encoding a secretory protein, p28 (Mercier et al., 1993, Mol. Biochem. Parasitol. 58:71–82). Examples of single copy *Neospora* genes include: (i) homologs of the *Toxoplasma* SAG1, GRA1 and GRA2 genes, identified using standard PCR methods based, for example, on the published *Toxoplasma* sequences; (ii) the gene encoding the major cell surface protein, NC-p43, of *N. caninum* tachyzoites (Hemphill, 1996, Infect. Immun. 64:4279–4287); and (iii) genes encoding the immunodominant 17-, 29-, 30- and 37 kDa excretory/secretory proteins (Bjerkas et al., 1994, Clin. Diag. Lab. Immun. 1:214–221). The 3' flanking region from the SAG1 gene may be used to provide a polyadenylation sequence. The vector backbone for insertion of the 5' promoter, ble gene, and 3' polyadenylation sequences may be any standard, commercially available plasmid, such as pBLUESCRIPT™ (Stratagene).

Once an appropriate vector is constructed, it is used to transform or transfect one or more cells from a parental strain of *Neospora*. The vector may be introduced into the cells in accordance with known techniques, including but not limited to electroporation, microinjection, viral transfection, liposome-mediated transfection, microprojectile bombardment, etc.

Once the vector is introduced into the *Neospora* cells, the presence, integration and maintenance of the introduced coding sequence into the host cell genome, or episomally, can be confirmed and monitored by standard techniques including, but not limited to, Southern hybridization analysis; PCR analysis, including reverse transcriptase-PCR (RT-PCR); immunological or colorimetric assay for the expected protein product; detecting the presence or absence of a marker gene function, such as appearance of a novel auxotrophy; or by detecting an attenuation in pathogenicity.

Examples of vector construction, transformation, selection of transformants, host cell expression, etc., as applied specifically to pathogenic protozoans, are described in the following publications, which are incorporated herein by reference: Seeber and Boothroyd, 1996, above; Titus et al., 1995, above; Messina et al., 1995, Gene, 165:213–217; Sibley et al., 1994, Proc. Natl. Acad. Sci. USA, 91:5508–5512; Donald and Roos, 1994, Mol. Biochem. Parasitol., 63:243–253; Kim et al., 1993, Science, 262: 911–914; Ryan et al., 1993, Proc. Natl. Acad. Sci. USA, 90:8609–8613; Soldati and Boothroyd,1993, Science, 260: 349–352; Eid and Sollner-Webb, 1991. Proc. Natl. Acad. Sci. USA, 88:2118–2121; LeBowitz et al., 1990, Proc. Natl. Acad. Sci. USA, 87:9736–9740; Lee and Van der Ploeg, 1990, Science, 250:1583–1586; Asbroek et al., 1990, Nature, 348:174–175; Cruz and Beverley, 1990, Nature, 348:171–173; and Laban et al., Nature, 343:572–574.

General techniques of genetic recombination, including vector construction, transformation, selection of transformants, host cell expression, etc., are further described in Maniatis et al, 1989, *Molecular Cloning, A Laboratory Manual*, Cold Spring Harbor Laboratory Press, Cold Spring Harbor, N.Y.; Ausubel et al., 1989, *Current Protocols in Molecular Biology*, Greene Publishing Associates & Wiley Interscience, N.Y.; Sambrook et al., 1989, *Molecular Cloning: A Laboratory Manual.* 2nd Ed., Cold Spring Harbor Laboratory Press, Cold Spring Harbor, N.Y.; Innis et al. (eds), 1995, *PCR Strategies*, Academic Press, Inc., San Diego, Calif.; and Erlich (ed), 1992, *PCR Technology*, Oxford University Press, New York, which are incorporated herein by reference.

After the attenuation step, cells that exhibit one or more indicators of attenuated pathogenicity are selected from the culture and clonally propagated after limiting dilution. Examples-of such indicators include, but are not limited to, appearance of a novel temperature-sensitivity or a novel auxotrophy in vitro, or a reduction in a virulence attribute such as infectivity or severity or rate of progression of one or more symptoms or conditions in a mammal after administration of cells of the strain as compared to infection with the parent strain, among others. A particular, non-limiting example of a temperature-sensitivity that is useful in practicing the invention is on in which cells of the attenuated strain will grow at 32° C., but not at 37° C. Such a temperature-sensitive strain will cause the lysis of infected host cells at 32° C., resulting in the appearance of lesions or plaques in a host cell monolayer. When grown at 37° C., the attenuated strain will not replicate sufficiently and will thus fail to produce plaques in host cell monolayers.

An attenuated strain of *Neospora* may be derived from any pathogenic strain of any species of the genus including, but not limited to, *N. caninum*. A non-limiting example of a particular pathogenic strain of *N. caninum* from which an attenuated strain may usefully be derived is strain NC-1 which is present in infected MARC145 monkey kidney cells from the American Type Culture Collection (ATCC), 12301 Parklawn Drive, Rockville, Md. 20852 USA (ATCC Accession No. CRL-12231). Strain NC-1 is also described in Dubey et al., 1988, J. Am. Vet. Med. Assoc. 193:1259–63, which publication is incorporated herein by reference. Alternatively, pathogenic strains of *Neospora* may be obtained from tissues, organs or body fluids of infected animals exhibiting clinical symptoms of neosporosis using standard isolation techniques described, for example, in the publications reviewed above. A non-limiting example of a live, attenuated strain derived from the NC-1 strain of *N. caninum* is NCTS-8 which is present in infected MARC145 monkey kidney cells from the ATCC (ATCC Accession No. CRL-12230).

Both parental strains and attenuated strains of *Neospora* may be cultured in vitro by infecting any receptive cell line, preferably a mammalian cell line, with tachyzoites of the strain according to known techniques described in the art. Mammalian cell lines in which tachyzoites of *Neospora* can be cultured include, for example, human foreskin fibroblasts (Lindsay et al., 1993, Am. J. Vet. Res. 54:103–106); bovine cardiopulmonary aortic endothelial cells (Marsh et al., 1995, above); and bovine monocytes (Lindsay and Dubey, 1989, above), among others. For example, tachyzoites of *N. caninum* may be cultured in monolayers of Hs68 human foreskin fibroblast cells (ATCC Accession No. CRL-1635) (Lindsay et al., 1993, above). Bradyzoites may be similarly cultured and manipulated.

Mammalian cell cultures can be grown, and cell cultures infected with *Neospora*can be maintained, in any one of several culture media described in the art. For example, stationary monolayer cultures of bovine cardiopulmonary aortic endothelial cells infected with tachyzoites of *N. caninum* may be grown in Dulb cco's Minimum Essential Medium (DMEM: Gibco Laboratories, N.Y.), supplemented with 10% (v/v) heat-inactivated fetal bovine serum (FBS) or adult equine serum (ES), 2 mM L-glutamine, 50 U/ml penicillin, and 50 $\mu$g/ml streptomycin (Conrad et al., 1993, above). Monolayers of Hs68 human foreskin fibroblast cells may be maintained in RPMI 1640 (Gibco) containing 2% (v/v) fetal bovine serum, 1.0 mM sodium pyruvate, $1\times10^4$ U/ml penicillin, $1\times10^4$ $\mu$g/ml streptomycin, $5\times10^{-2}$ mM 2-mercaptoethanol and 0.3 mg/ml L-glutamine (maintenance medium). Monolayer cultures of Hs68 human foreskin fibroblast cells infected with *Neospora* may be maintained in identical media, but in which the fetal bovine serum is increased to 10% (v/v) (growth medium). Attenuated strains of *Neospora* having novel auxotrophies will require appropriate modification to the culture medium to support growth, as known in the art.

*Neospora*-infected monolayer cultures of mammalian cells are typically maintained under standard tissue culture conditions such as, for example, at 37° C. and 5% $CO_2$. Tachyzoites are generally passaged to uninfected monolayer cultures when 70–90% of the mammalian cells in the culture have become infected, which may be determined microscopically using standard techniques. Tachyzoites may be collected from the infected mammalian cell cultures by lysing the host cells using any standard technique that allows the tachyzoites to retain viability, and collecting the tachyzoites by filtration or by centrifugation, for example.

Preparation and use of Vaccines

The present invention provides vaccines against neosporosis, comprising an immunologically effective amount of live cells of a strain derived from a pathogenic parent strain of a species of *Neospora*, which cells exhibit attenuated pathogenicity compared to those of the parent strain but which are capable of triggering an immune response that protects the mammal against neosporosis when administered as a live vaccine, and a veterinarily acceptable carrier.

The present invention further provides methods for preparing a vaccine that protects a mammal against neosporosis, comprising modifying cells from a pathogenic parent strain of a species of *Neospora*; selecting and clonally propagating those modified cells that exhibit attenuated pathogenicity compared to cells of the parent strain but which are capable of triggering an immune response in the mammal that protects against neosporosis when administered in a live vaccine; and combining an immunologically effective amount of the attenuated cells with a veterinarily acceptable carrier in a form suitable for administration as a live vaccine to the mammal.

The present invention further provides methods of vaccinating a mammal against neosporosis, comprising administering to the mammal an immunologically effective amount of a vaccine comprising live cells of a strain derived from a pathogenic parent strain of a species of *Neospora*, which cells exhibit attenuated pathogenicity compared to those of the parent strain but which are capable of triggering an immune response that protects the mammal against neosporosis when administered as a live vaccine, and a veterinarily acceptable carrier.

The vaccine of the invention comprises live cells of an attenuated strain of *Neospora*, either as the sole antigenic component or in combination with one or more other antigens that trigger an immune response that protects a mammal against a disease or pathological condition which may or may not be related to neosporosis. Thus, the present invention further provides combination vaccines, comprising an immunologically effective amount of live cells of a strain derived from a pathogenic parent strain of a species of *Neospora*, which cells exhibit attenuated pathogenicity compared to those of the parent strain but which are capable of triggering an immune response that protects the mammal against neosporosis when administered as a live vaccine; one or more other antigens that trigger an immune response that protects the mammal against a disease or a pathological condition; and a veterinarily acceptable carrier. The combination vaccines may further comprise, one or more other components including, for example, an adjuvant.

The vaccine is conventionally administered parenterally, for example, either by subcutaneous or intramuscular injection. However, the vaccine may also be administered by intraperitoneal or intravenous injection, or by other routes, including orally, intransally, rectally or vaginally, and where the vaccine is so administered, a veterinarily acceptable carrier is appropriately selected. The vaccine may simply comprise attenuated cells in culture fluid, which are administered directly to the mammal. Alternatively, the vaccine may comprise attenuated cells combined with a veterinarily or pharmaceutically acceptable carrier selected from those known in the art based on the route of administration and its ability to maintain cell viability. Non-limiting examples of such carriers include water, saline, buffered vehicles and the like. Suitable other vaccine vehicles and additives are known, or will be apparent, to those skilled in the art. See, e.g., Remington's *Pharmaceutical Science,* 18th ed., 1990, Mack Publishing, which is incorporated herein by reference.

The vaccine may further comprise one or more other components such as an immunomodulatory agent including, for example, interleukin-1, or another immuno-enhancing substance such as a veterinarily acceptable adjuvant. Non-limiting examples of adjuvants include Freund's complete and incomplete adjuvants, mineral gels including, for example, aluminum hydroxide, and oil-in-water or water-in-oil formulations. Immunomodulatory agents are selected based on their ability to maintain both viability of the attenuated *Neospora* cells and ability of the cells to trigger a protective immune response in the vaccinated mammal.

Non-limiting examples of oil-in-water formulations that are useful as adjuvants in the vaccines of the invention include emulsions 1–3, as follows. Emulsion 1 consists of: (a) ME6201 (5% v/v squalene, 0.1% v/v vitamin E, and 0.8% v/v Tween™ 80 dispersant); (b) Quil A (QA) saponin preparation (Superfos) (200 μg/ml); and (c) cholesterol (chol.) (100 μg/ml). Emulsion 2 consists of: (a) ME6201; and (b) Avridine lipoidal amine (1 mg/ml). Emulsion 3 consists of ME6210 (5% v/v squalene, 1.0% v/v vitamin E, and 0.8% v/v Tween™ 80 dispersant).

An effective dosage may be determined by conventional means, starting with a low dose of attenuated cells and then increasing the dosage while monitoring the effects, and systematically varying the dosage as well. Numerous factors may be taken into consideration when determining an optimal dosage per animal. Primary among these is the species, the size of the animal, the age of the animal, the general condition of the animal, the presence of other drugs in the animal, the virulence of a particular strain of *Neospora* against which the animal is being vaccinated, and the like. The actual dose would preferably be chosen after consideration of the results of other animal studies.

Vaccine regimens are selected also based on the above-described factors. Animals may be vaccinated at any time, including just prior to or at the time of breeding. Supplemental administrations, or boosters, may be required for full protection. One method of detecting whether adequate immune protection has been achieved is to determine seroconversion and antibody titers in the animal after vaccination. Thus, the vaccine of the invention may be administered at any time during the life of a particular animal to be vaccinated, depending upon several factors, including, for example, the timing of an outbreak of neosporosis among other animals, etc. The vaccine may be administered to animals of weaning age or younger, or to more mature animals, for example, as a pre-breeding vaccine to protect against *Neospora*-related congenital disease or abortion. Effective vaccination may require only a primary vaccination, or a primary vaccination with one or more booster vaccinations. Booster vaccinations may be administered at any time after primary vaccination depending, for example, on the immune response after primary vaccination, the severity of the outbreak, the virulence of the strain of *Neospora* causing the outbreak, the health of the vaccinate, etc. The timing of vaccination and the number of boosters, if any, will preferably be determined by a veterinarian based on analysis of all relevant factors, some of which are described above.

The *Neospora* cells used in the vaccine are preferably tachyzoites, but may instead be bradyzoites, or oocysts, or some combination thereof. The concentration of attenuated cells in the vaccine preferably ranges from about $1\times10^3$/ml to about $1\times10^8$/ml, and more preferably from about $2\times10^6$/ml to about $2\times10^7$/ml. A suitable dosage size ranges from about 0.5 ml to about 1.0 ml. Generally, on a per-dose basis, the number of attenuated cells administered to an animal is preferably from about $2\times10^4$ to about $2\times10^8$; more preferably from about $2\times10^5$ to about $2\times10^7$; and most preferably from about $1\times10^6$ to about $1\times10^7$.

The vaccine of the invention protects a mammal against infection or disease caused by *Neospora*. The vaccine is useful to protect both pregnant and non-pregnant mammals including, but not limited to, bovine, ovine, caprine, canine and equine species, against infection, clinical disease or abortion resulting from neosporosis. The term "protection" is used broadly and is not limited to absolute prevention of infection by *Neospora*, but includes a reduction in infectivity, or in the severity of a disease or condition resulting from infection, including a detectable reduction in one or more of the pathological effects or symptoms resulting from infection, or a detectable reduction in the rate of progression of one or more of such pathological effects or symptoms. The vaccine of the invention is also safe, i.e., it does not cause disease or significant side effects in the vaccinated mammal.

The following examples are offered to further illustrate, but not limit, the compositions and methods of the invention.

EXAMPLE 1

Establishment of Temperature-Sensitive Strains of *N. caninum* and Analysis of Pathogenicity in BALB/c Mice The objective of this study was to establish temperature-sensitive strains of *N. caninum* (NCTS), and to test the pathogenicity of these strains by analyzing serum antibody response, tissue cyst and brain lesion production, and the development of clinical symptoms in BALB/c mice, which are known to be highly susceptible to neosporosis.

Materials and Methods

Tachyzoites of the NC-1 strain of *N. caninum* (Dubey et al., 1988, above) were cloned twice by limiting dilution and maintained at 37° C., as described (Lindsay and Dubey, 1989, above). The tachyzoites were propagated in 25 $cm^2$ flasks and cloned in 96-well plates containing monolayers of Hs68 human foreskin fibroblast cells (ATCC Accession No. CRL-1635) (Lindsay et al., 1993, above). The Hs68 cells were previously grown in RPMI 1640 containing 2% (v/v) fetal bovine serum, 1.0 mM sodium pyruvate, $1\times10^4$ U/ml penicillin, $1\times10^4$ μg/ml streptomycin, $5\times10^{-2}$ mM 2-mercaptoethanol and 0.3 mg/ml L-glutamine (maintenance medium). Infected cell culture monolayers were maintained in identical medium, but in which fetal bovine serum was increased to 10% (v/v) (growth medium). A clone was isolated and designated in the laboratory as the NC-1–2C line, but is referred to hereinafter simply as the NC-1 strain.

Tachyzoites of the NC-1 strain were mutagenized by exposure to 0.5 μM N-methyl-N'-nitro-N-nitrosoguanidine (Sigma) in growth medium for 24 hr, and then grown at 32.5° C. for 3 mos in Hs68 cells in maintenance medium, after which tachyzoites were cloned by limiting dilution. Twelve clones were initially isolated. Three clones, designated as NCTS-4, NCTS-8, and NCTS-12 (NCTS=*N. caninum*, temperature-sensitive), were selected for further study after being maintained in Hs68 cells in continuous culture at 32.5° C. for >8 mos in maintenance medium.

Serological testing of mice was conducted as follows. An indirect immunofluorescent antibody test (IFAT) (Dubey et al., 1988, above) was used to analyze sera from mice for the presence of antibodies directed against *N. caninum*. Mouse sera were obtained immediately prior to challenge inoculation in vaccination studies. Serum was also obtained from all mice that survived pathogenicity experiments. Sera were examined at doubling dilutions beginning at 1:50 and end-point titrated. Tachyzoites were used as antigen. Positive samples exhibited a complete tachyzoite surface fluorescence. Negative samples exhibited no fluorescence or only anterior end fluorescence.

The presence of lesions in the brains of mice challenged with different strains of *N. caninum* was determined as follows. The brain from each mouse was removed at necropsy, and a first half was fixed in 10% v/v neutral buffered formalin solution for histopathological examination. Tissue sections were prepared using routine histological techniques, and stained with hematoxylin and eosin to detect the presence of lesions microscopically.

Lesion scoring of hematoxylin- and eosin-stained brain tissue sections was conducted according to the criteria described in Lindsay et al., 1995, J. Parasitol. 81:313–315.

-continued

| | Score |
|---|---|
| Number of inflammatory/necrotic foci | |
| No foci | 1 |
| 1–5 foci | 2 |
| 6–10 foci | 3 |
| >10 foci | 4 |
| Average size of foci | |
| None | 1 |
| 100–200 μm | 2 |
| 200–500 μm | 3 |
| >500 μm | 4 |
| Severity of lesions | |
| No lesions | 1 |
| slight | 2 |
| mild | 3 |
| moderate | 4 |
| marked | 5 |

A mean lesion score was obtained using the three values listed above. A normal, non-infected mouse brain would have a mean lesion score of 3.0. Mean lesion scores were evaluated using a Kruskal-Wallis nonparameteric test, and distribution free multiple comparison methods. The number of mice in each group with lesions was examined using Fisher's exact test. Statistical significance was established at a cutoff of $P<0.05$.

Sections of brain from each mouse were also examined using a murine monoclonal antibody, 6G7, specific for *N. caninum*, in conjunction with an avidin-biotin peroxidase complex (ABC) immunohistochemical test, to detect *N. caninum* stages (Cole et al., 1993, J. Vet. Diag. Invest. 5:574–589).

The second half of each mouse brain was digested in acid-pepsin and used to inoculate mammalian cell cultures to detect the presence of tissue cysts of *N. caninum*. To digest, the second half of the mouse brain was placed in 3 ml of Hank's balanced salt solution (HBSS) and passed twice through a syringe with a 23 gauge needle. Three ml of acid-pepsin solution (0.52 g pepsin, 0.50 g NaCl, 98.6 ml $dH_2O$, 1.4 ml conc. HCl, pH 0.8), was added to the homogenate and incubated for 10 min at 37° C. in a water bath. The acid pepsin solution was removed by centrifugation and the pellet, representing the entire second brain half, was inoculated into a single 25 $cm^2$ tissue culture flask containing a monolayer of Hs68 human foreskin fibroblast cells cultured as described above. After 30 min, the inoculum was removed and the Hs68 cell monolayer was washed and incubated in fresh maintenance medium as above. Cell cultures were then examined for 30 days to detect the presence of *N. caninum* (Lindsay and Dubey, 1989, above).

The pathogenicity of NC-1 and the three selected NCTS strains, i.e., NCTS-4, NCTS-8, and NCTS-12, of *N. caninum* were determined as follows. BALB/c mice (8 wk, female) (Harlan Sprague Dawley (HSD)) were inoculated subcutaneously with HBSS (control), or with $5\times10^5$ tachyzoites of either the NC-1, NCTS-4, NCTS-8, or NCTS-12 strain of *N. caninum* in HBSS (0.5 to 1.2 ml total volume). Surviving mice were examined at necropsy 42 or 56 days post-inoculation (PI) (see Table 1). Serum was collected from surviving mice at necropsy. Brains of these mice were examined for lesion scoring and immunohistology, and one half of each brain was used for acid-pepsin digestion to determine the presence of tissue cysts, as described above.

TABLE 1

Results of inoculating BALB/c mice with tachyzoites of NCTS-4, NCTS-8, NCTS-12 or NC-1 strains of *N. caninum.*

| Treatment Group | No. Mice | *N. caninum* Strain | Result |
|---|---|---|---|
| 1 | 4 | HBSS (control) | No mortality. |
| 2 | 5 | NCTS-4 | No mortality. |
| 3 | 5 | NCTS-4 | No mortality. |
| 4 | 5 | NCTS-8 | No mortality. |
| 5 | 5 | NCTS-8 | No mortality. |
| 6 | 5 | NCTS-12 | No mortality. |
| 7 | 5 | NCTS-12 | No mortality. |
| 8 | 5 | NC-1 | Clinical neosporosis developed at about 16 days PI; mice were less active than in groups 1–7; with rough hair coats. Two mice were euthanized because of neosporosis at 34 days PI; one additional mouse died 39 days PI. |
| 9 | 5 | NC-1 | Clinical signs same as in group 8; mice found dead on days 26, 30, 32 and 41 PI. |

TABLE 2

Mean lesion scores of BALB/c mice inoculated with different strains of *N. caninum.*

| Treatment Group | No. mice with lesions/No. examined/No. survived | Mean Lesion Score |
|---|---|---|
| 1 (HBSS-control) | 0/4/4 | 3.00 |
| 2 + 3 (NCTS-4) | 4/10/10[a] | 4.80 |
| 4 + 5 (NCTS-8) | 6/10/10[a] | 5.50 |
| 6 + 7 (NCTS-12) | 5/10/10[a] | 4.90 |
| 8 + 9 (NC-1) | 8/8/3[a,b] | 9.38[a,b] |

[a]= significantly different from control (HBSS) ($P < 0.05$).
[b]= significantly different from NCTS-4, NCTS-8, and NCTS-12 ($P < 0.05$).

TABLE 3

Reciprocal antibody titers in mouse serum.

| | Reciprocal Antibody Titer | | | | |
|---|---|---|---|---|---|
| Treatment Group | <50 | 800 | 1,600 | 3,200 | 6,400 |
| 1 (HBSS-control) 42 Days PI | 2 | — | — | — | — |
| 1 (HBSS) 56 Days PI | 2 | — | — | — | — |
| 2 (NCTS-4) 42 Days PI | — | 1 | 4 | — | — |
| 3 (NCTS-4) 56 Days PI | — | — | 5 | — | — |
| 4 (NCTS-8) 42 Days PI | — | — | 3 | 2 | — |
| 5 (NCTS-8) 56 Days PI | — | — | 3 | 2 | — |
| 6 (NCTS-12) 42 Days PI | — | — | 3 | 2 | — |
| 7 (NCTS-12) 56 Days PI | — | — | 4 | 1 | — |
| 8 (NC-1) 56 Days PI | — | — | 2 | — | — |
| 9 (NC-1) 56 Days PI | — | — | 1 | — | — |

Results

Clinical neosporosis and mortality occurred only in BALB/c mice inoculated with the NC-I strain (Table 1). Only three out of 10 BALB/c mice survived the NC-1 strain infection. The NCTS-4, NCTS8, and NCTS-12 strains did not cause mortality in BALB/c mice.

Mean lesion scores are presented in Table 2. Lesions were found in brains of some mice inoculated with the NCTS strains, but mean lesion scores were not statistically significant when compared to the control (HBSS). A significant difference in mean lesion scores and numbers of mice with lesions was found when mice inoculated with the NC-1 strain were compared to mice inoculated with HBSS (control) or with any of the NCTS strains of *N. caninum.*

Serum antibody titers are presented in Table 3. Significant IFAT titers (≧400) were detected in all mice challenged (30/30) with NCTS strains. This indicates that NCTS strains are capable of stimulating a B-cell response in an immunologically intact, but genetically susceptible, animal. IFAT titers in NCTS-challenged mice were equal to, or in some cases higher than, those in NC-1 challenged mice.

Tissue cysts were not detected in any of the brain halves examined using the acid-pepsin digestion technique described above. This indicates that tissue cysts, if present, are few in number in mice inoculated with the NCTS or NC-1 strains of *N. caninum.*

EXAMPLE 2

Analysis of Pathogenicity of NCTS Strains of *N. caninum* in HSD:ICR Outbred Mice The objective of this study was to determine the pathogenicity of NCTS strains of *N. caninum* in HSD:ICR outbred mice, which are immunocompetent and more resistant to *Neospora* than inbred BALB/c mice.

Materials and Methods

HSD:ICR mice (4 wk, female) were used in this experiment. All HSD:ICR mice, except for controls, were inoculated with $5\times10^5$ tachyzoites of the appropriate strain of *N. caninum* in HBSS (total volume 0.5 to 1.2 ml). Control mice were inoculated with HBSS only. All surviving mice were sacrificed 56 days PI. Serum was collected for IFAT testing. Brains from these mice were collected and a first half was used for lesion scoring and immunohistology, as above. The second half of each brain was used in the acid-pepsin digestion to detect tissue cysts, as described above.

Results

None of the *N. caninum* strains tested, including NC-1, caused mortality in HSD:ICR mice (Table 4), and no significant differences were observed in numbers of mice with lesions or in the mean lesions scores compared to non-challenged controls (Table 5). No brain tissue cysts were observed in histological or ABC-stained sections. No parasites were isolated in cell cultures.

TABLE 4

| Results of inoculating HSD:ICR mice with tachyzoites of NC-1, NCTS-4, NCTS-8 or NCTS-12 strains of *N. caninum.* | | | |
|---|---|---|---|
| Treatment Group | No. Mice | *N. caninum* Strain | Result |
| 10 | 5 | HBSS (control) | No mortality. |
| 11 | 5 | NC-1 | No mortality. |
| 13 | 5 | NCTS-4 | No mortality. |
| 14 | 5 | NCTS-8 | No mortality. |
| 15 | 5 | NCTS-12 | No mortality. |

TABLE 5

| Mean lesion scores of HSD:ICR mice inoculated with various strains of *N. caninum.* | | |
|---|---|---|
| Treatment Group | No. mice with lesions/ No. examined/No. survived | Mean Lesion Score[a] |
| 10 (HBSS-control) | 0/5/5 | 3.0 |
| 11 (NC-1) | 3/5/5 | 6.0 |
| 13 (NCTS-4) | 0/5/5 | 3.0 |
| 14 (NCTS-8) | 1/5/5 | 4.0 |
| 15 (NCTS-12) | 0/5/5 | 3.0 |

[a]= No significant differences were observed between treatment groups.

TABLE 6

| Reciprocal antibody titers in mouse serum.[a] | | | | | | |
|---|---|---|---|---|---|---|
| Treatment | Reciprocal Antibody Titer | | | | | |
| Group | <50 | 400 | 800 | 1,600 | 3,200 | 6,400 |
| 10 (HBSS-control) | 5 | — | — | — | — | — |
| 11 (NC-1) | — | — | — | 2 | 3 | — |
| 13 (NCTS-4) | — | 1 | 3 | 1 | — | — |
| 14 (NCTS-8) | 1 | — | 2 | 1 | 1 | — |
| 15 (NCTS-12) | 1 | — | 3 | 1 | — | — |

[a]= All titers were determined at day 56 PI.

Antibody titers of surviving mice are presented in Table 6. Significant IFAT titers (≧400) were detected in the majority of mice (13/15) challenged with the NCTS strains, indicating that these strains are capable of inducing a B-cell response in immunologically intact, but genetically resistant, animals.

Tissue cysts were not detected in the portion of brain examined histologically, immunohistologically, or by using the acid-pepsin digestion procedure. These results confirm those presented in Example 1, above, using BALB/c mice.

EXAMPLE 3

Analysis of Pathogenicity of NCTS Strains of *N. caninum* in Immunosuppressed HSD:ICR Mice A first objective of this study was to determine the pathogenicity of NCTS strains of *N. caninum* in immunosuppressed HSD:ICR mice. A second objective of this study was to determine if reversion to pathogenicity occurs after in vitro passage of NCTS strains of *N. caninum* at 37° C.

Materials and Methods

HSD:ICR mice (4 wk, female) were immunosuppressed by intramuscular administration of 2 mg m thylprednisolone acetate (MPA) (Upjohn-Pharmacia) on days −7, 0, and 7 PI. See Lindsay and Dubey, 1989, J. Parasitology 75:772–779.

The immunosuppressed HSD:ICR mice were inoculated on day 0 with $2\times10^5$ tachyzoites of either the NC-1, NCTS4, NCTS-8, or NCTS-12 strains, or one of the potential reversion controls, designated NCTS-4-37, NCTS-8-37, or NCTS-12-37, in HBSS (total volume 0.5 to 1.2 ml). The mice were subsequently examined serologically, histologically, and clinically, as described above.

NCTS-4, NCTS8, and NCTS-12 clones were examined for reversion to pathogenicity by growth at 37° C. for 88 days (25 cell culture passes), followed by inoculation in immunosuppressed HSD:ICR mice (potential reversion strains are designated as NCTS4-37, NCTS8-37, NCTS-12-37).

Results

The NC-1, NCTS4-37, and NCTS-12-37 strains of *N. caninum* caused 100% mortality in immunosuppressed HSD:ICR mice (Table 7). The NCTS4, NCTS-8, NCTS-12, and NCTS-8-37 strains were less pathogenic toward immunosuppressed HSD:ICR mice and caused only from 0 to 20% mortality. Mean lesion scores are presented in Table 8. No tachyzoites were detected in acid-pepsin digests from any mice examined at necropsy 56 days PI.

Antibody titers of surviving mice are presented in Table 9. Significant IFAT titers (≧800) were detected in NCTS4, -8, and -12, and NCTS-8-37 mice at day 56 post-challenge, indicating that these strains are capable of stimulating a Bell response in an immunosuppressed, but genetically resistant, animal.

TABLE 7

| Results of inoculating immunosuppressed HSD:ICR mice with tachyzoites of NC-1, NCTS-4, NCTS-8, NCTS-12, or potential reversion strains of *N. caninum.* | | | |
|---|---|---|---|
| Treatment Group | No. Mice | *N. caninum* Strain | Result |
| 16 | 5 | HBSS (control) | No mortality. |
| 17 | 5 | NC-1 | 3 mice died or were euthanized* on day 20, and one mouse died on each of days 22 and 23 PI. |
| 18 | 5 | NCTS-4 | No mortality. |
| 19 | 5 | NCTS-8 | 1 mouse euthanized 20 days PI.* |
| 20 | 5 | NCTS-12 | 1 mouse died 22 days PI. |
| 21 | 5 | NCTS-4-37 | All mice died or were euthanized at 13, 14 (2), 16 and 21 days PI.* |
| 22 | 5 | NCTS-8-37 | 1 mouse died 29 days PI. |
| 23 | 5 | NCTS-12-37 | 1 mouse died and 4 were euthanized 14 days PI.* |

*= Mice that were moribund due to clinical encephalitic neosporosis were euthanized for humane reasons.

TABLE 8

| Mean lesion scores of immunosuppressed HSD:ICR mice inoculated with various strains of *N. caninum*. | | |
|---|---|---|
| Treatment Group | No. mice with lesions/No. examined/No. survived | Mean Lesion Score |
| 16 (HBSS-control) | 0/5/5 | 3.0 |
| 17 (NC-1) | 4/4/0[a] | 9.8[a] |
| 18 (NCTS-4) | 1/5/5 | 3.6 |
| 19 (NCTS-8) | 2/5/4 | 5.2 |
| 20 (NCTS-12) | 3/5/4 | 6.2 |
| 21 (NCTS-4-37) | 3/3/0[a] | 8.7 |
| 22 (NCTS-8-37) | 5/5/4[a] | 8.2 |
| 23 (NCTS-12-37) | 4/4/0[a] | 9.5[a] |

[a]= significantly different from control (Group 16) ($P < 0.05$).

TABLE 9

| Reciprocal antibody titers in mouse serum.[a] | | | | | | | |
|---|---|---|---|---|---|---|---|
| Treatment | Reciprocal Antibody Titer | | | | | | |
| Group | <50 | 100 | 800 | 1,600 | 3,200 | 6,400 | 12,800 |
| 16 (HBSS-control) | 5 | — | — | — | — | — | — |
| 18 (NCTS-4) | — | 1 | 1 | 1 | 1 | 1 | — |
| 19 (NCTS-8) | — | — | — | 2 | 1 | 1 | — |
| 20 (NCTS-12) | — | — | — | 1 | 2 | 1 | — |
| 22 (NCTS-8-37) | — | — | — | — | 1 | 2 | 1 |

[a]= All titers were determined at day 56 PI.

The NCTS strains were less pathogenic in immunosuppressed HSD:ICR mice than the NC-1, NCTS4-37 and NCTS-12-37 strains. The relatively high survival rate (4/5) of mice inoculated with the NCTS8-37 reversion strain compared with the 100% mortality rate of mice inoculated with the NCTS-4-37 or NCTS-12-37 reversion strains indicates that the NCTS-8-37 reversion strain retained attenuated pathogenicity following serial passage at 37° C. Based on this demonstrated retention of attenuated pathogenicity, the NCTS-8 strain of *N. caninum* was selected as a potential vaccine candidate and used in further studies, as described below.

EXAMPLE 4

Vaccination of BALB/c Mice Against *N. caninum*-Induced Encephalitis

A first objective of this study was to determine if vaccination with a live, temperature-sensitive strain of *N. caninum* can provide protection against disease caused by subsequent challenge with a pathogenic strain, e.g., NC-1, of *N. caninum*. A second objective of this study was to determine the level of protection provided by vaccination of BALB/c mice with killed (frozen) NCTS8 tachyzoites that were subsequently challenged with the NC-1 strain of *N. caninum.*

Materials and Methods

BALB/c mice (9 wk, female) were vaccinated by subcutaneous injection with either HBSS (control) (0.5 ml), or $5\times10^5$ living tachyzoites of the NCTS8 strain in HBSS (0.5 ml), or $2\times10^6$ killed (frozen) tachyzoites in HBSS (0.5 ml) (Table 10). The vaccinates were boosted 21 days PI with the same material as in the primary injection. The mice were then challenged by subcutaneous administration of $1\times10^6$ tachyzoites of the NC-1 strain of *N. caninum* in HBSS, or with HBSS alone (control) (total volume 0.5 ml), 14 days after the booster.

IFAT was used to test sera from mice that survived the experiment for the presence of antibodies against *N. caninum*, as described above. The brain from each mouse was removed at necropsy. The first half was used for histopathology and immunohistology, and the second half was used for acid-pepsin digestion, as d scribed above. Viability of tachyzoites after freezing was determined by inoculating monolayer cultures of Hs68 human foreskin fibroblast cells, as described above.

Results

None of the mice in any test group died after primary or booster vaccination. Two of 10 mice vaccinated with HBSS (controls), and 3 of 10 mice vaccinated with killed NCTS-8 tachyzoites, died after being challenged with NC-1 tachyzoites. Mean lesion scores of mice that survived are presented in Table 11.

Reciprocal antibody titers of surviving mice are presented in Table 12. Significant IFAT titers (≧800) were detected in mice vaccinated with live NCTS-8 tachyzoites following the booster, confirming previous results described above. In contrast, no significant IFAT titers were present in any mice vaccinated with killed NCTS-8 tachyzoites prior to challenge, demonstrating that killed tachyzoites fail to induce a significant antibody response in a genetically susceptible host.

*N. caninum* tachyzoites were isolated from cell cultures inoculated with acid-pepsin-digested brain tissue from two sham-vaccinated, challenged mice (group 24, mice nos. 1 and 2), and from one mouse vaccinated with killed, NCTS-8 tachyzoites (group 31, mouse no. 5). No tachyzoites were isolated from cultures inoculated with brain tissue from any other mice.

TABLE 10

| Protocol for vaccination and challenge of BALB/c mice. | | | |
|---|---|---|---|
| Treatment Group | No. Mice | Vaccination & Booster | Challenge |
| 24 | 5 | HBSS | NC-1 |
| 25 | 5 | HBSS | NC-1 |
| 26 | 5 | NCTS-8 (Live) | HBSS |
| 27 | 5 | NCTS-8 (Live) | HBSS |
| 28 | 5 | NCTS-8 (Live) | NC-1 |
| 29 | 5 | NCTS-8 (Live) | NC-1 |
| 30 | 5 | NCTS-8 (Killed) | NC-1 |
| 31 | 5 | NCTS-8 (Killed) | NC-1 |

TABLE 11

Mean lesion scores of vaccinated, challenged BALB/c mice.

| Treatment Group | No. mice with lesions/No. examined/No. survived | Mean lesion score |
|---|---|---|
| 24 + 25 | 8/8/8 | 9.3 |
| 26 + 27 | 1/10/10 | 3.4[a,b] |
| 28 + 29 | 1/10/10 | 3.3[a,b] |
| 30 + 31 | 6/7/7 | 7.7 |

[a]= significantly different from groups 24 + 25 ($P < 0.05$).
[b]= significantly different from groups 30 + 31 ($P < 0.05$).

TABLE 12

Reciprocal antibody titers in mouse serum pre- and post-challenge.

| Treatment Group | Pre- or Post Challenge | Reciprocal Antibody Titer <50 | 50 | 100 | 400 | 800 | 1,600 | 3,200 | 6,400 |
|---|---|---|---|---|---|---|---|---|---|
| 24 + 25 (HBSS-control) | Pre- | 10 | — | — | — | — | — | — | — |
| 24 + 25 (HBSS-control) | Post- | — | — | — | — | — | 1 | 4 | 3 |
| 26 + 27 (NCTS-8, live; HBSS) | Pre- | — | — | — | 1 | 4 | 4 | 1 | — |
| 26 + 27 (NCTS-8, live; HBSS) | Post- | — | — | — | — | 3 | 4 | 3 | — |
| 28 + 29 (NCTS-8 live; NC-1) | Pre- | — | — | — | — | 1 | 9 | — | — |
| 28 + 29 (NCTS-8 live; NC-1) | Post- | — | — | — | — | 1 | 8 | 1 | — |
| 30 + 31 (NCTS-8 killed; NC-1) | Pre- | 6 | 2 | 2 | — | — | — | — | — |
| 30 + 31 (NCTS-8 killed; NC-1) | Post- | — | — | — | 1 | 1 | 2 | 2 | 1 |

Mice vaccinated with live tachyzoites of the NCTS8 strain of *N. caninum* did not die or develop clinical disease symptoms. Mice vaccinated with live tachyzoites of the NCTS-8 strain and subsequently challenged with tachyzoites of the NC-1 strain (Table 11, groups 28+29) had lesion scores that were almost identical to those of mice vaccinated with live tachyzoites of the NCTS-8 strain followed by administration of HBSS (Table 11, groups 26+27). This indicates that vaccination with live tachyzoites of the NCTS-8 strain provides substantial protection against disease caused by infection with the NC-1 strain of *N. caninum*. Vaccination of mice with killed tachyzoites of the NCTS-8 strain offered little protection from neosporosis (Table 11, groups 30+31).

EXAMPLE 5

Vaccination of BALB/c Mice with a Low Dose of the NCTS-8 Strain of *N. Caninum*

The objective of this study was to determine if a low dose, i.e., $5\times10^4$ tachyzoites, of the NCTS-8 strain of *N. caninum* can provide protection against a subsequent challenge infection.

Materials and Methods

BALB/c mice (7 wk, female) were vaccinated subcutaneously either with HBSS, or with $5\times10^4$ tachyzoites from the NCTS-8 strain of *N. caninum* in HBSS (0.5 ml) (Table 13). This dose of tachyzoites is one-tenth the amount used in previous examples. The mice were boosted 21 days PI with the same material as in the primary injection. The mice were then challenged 14 days after the booster with $1\times10^6$ tachyzoites of the NC-1 strain of *N. caninum.*

IFAT was used to test sera from mice that survived the experiment for antibodies against *N. caninum*, as described above. The brain from each mouse was removed at necropsy. A first half was used for histopathology and immunohistology, and the remaining second half was used for the acid-pepsin digestion, as described above.

Results

One control mouse (administered only HBSS) died after subsequent challenge with tachyzoites of the NC-1 strain of *N. caninum*. None of the mice vaccinated with the low dose of tachyzoites of the NCTS8 strain of *N. caninum* died after subsequent challenge with tachyzoites of the NC-1 strain. Mean lesion scores and numbers of mice with lesions were significantly higher in control mice sham-vaccinated only with HBSS than in mice vaccinated with a low dose of the NCTS-8 strain (Table 14). Reciprocal antibody titers are shown in Table 15.

TABLE 13

Protocol for low dose vaccination and challenge of BALB/c mice.

| Treatment Group | No. Mice | Vaccination & Booster | Challenge |
|---|---|---|---|
| 32 | 5 | HBSS | NC-1 |
| 36 | 5 | NCTS-8 ($5 \times 10^4$ tachyzoites) | NC-1 |

TABLE 14

Mean lesion scores in mice.

| Treatment Group | No. surviving mice bearing lesions/No. mice surviving | Mean lesion score |
|---|---|---|
| 32 (HBSS/NC-1) | 4/4 | 10.25[a] |
| 36 (NCTS-8/NC-1) | 2/5 | 4.50 |

[a]= significantly different from group 36 ($P < 0.05$).

TABLE 15

Reciprocal antibody titers in mouse serum prior to challenge inoculation.

| | Reciprocal Antibody Titer | | | | | |
|---|---|---|---|---|---|---|
| Treatment Group | <50 | 400 | 800 | 1,600 | 3,200 | 6,400 |
| 32 (HBSS) anti-Neospora titer | 10 | — | — | — | — | — |
| 36 (NCTS-8) anti-Neospora titer | — | 3 | 4 | 3 | — | — |

EXAMPLE 6

Efficacy of Vaccines with and without Adjuvant

The objective of this study was to determine the effect of adding an adjuvant to a modified-live *Neospora* vaccine and the degree of protection obtained therefrom against neosporosis.

Materials and Methods

Previous in vitro results (data not shown) indicated that tachyzoites of at least one modified-live *N. caninum* strain, i.e., NCTSB, retained partial viability and infectivity in vitro when co-incubated with one of several different oil-in-water formulations. Based on these in vitro results, three specific formulations were selected for in vivo evaluation as adjuvants.

Groups of ten 15 wk female BALB/c mice were vaccinated subcutaneously (0.2 ml) on days 0 (primary vaccination) and 21 (booster) PI, either with HBSS alone (control), or with $5\times10^5$ tachyzoites of the NCTS-8 strain of *N. caninum* in HBSS, or with $5\times10^5$ tachyzoites of the NCTS-8 strain of *N. caninum* in one of the following three oil-in-water emulsions.

Emulsion 1 consisted of: (a) ME6201 (5% v/v squalene, 0. 1% v/v vitamin E, and 0.8% v/v Tween™ 80 dispersant); (b) Quil A saponin preparation (QA) (Superfos) (200 $\mu$g/ml); and (c) cholesterol (chol.) (100 $\mu$g/ml).

Emulsion 2 consisted of: (a) ME6201; and (b) Avridine lipoidal amine (1 mg/ml).

Emulsion 3 consisted of ME6201 (5% v/v squalene, 1.0% v/v vitamin E, and 0.8% v/v Tween™ 80 dispersant).

TABLE 16

Protocol for testing vaccine formulations with and without adjuvant.

| Treatment Group | Vaccine | Emulsion |
|---|---|---|
| 38 | HBSS | none |
| 39 | NCTS-8 | none |

TABLE 16-continued

Protocol for testing vaccine formulations with and without adjuvant.

| Treatment Group | Vaccine | Emulsion |
|---|---|---|
| 40 | HBSS | 1 |
| 41 | NCTS-8 | 1 |
| 42 | HBSS | 2 |
| 43 | NCTS-8 | 2 |
| 44 | HBSS | 3 |
| 45 | NCTS-8 | 3 |

On day 35 PI, all mice were challenged by a subcutaneous administration of $1\times10^8$ tachyzoites of the NC-1 strain of *N. caninum* in HBSS (0.2 ml). Groups of 3 to 5 mice were sacrificed on days 49 and 63 PI for evaluation of vaccine efficacy.

Beginning on day 0, disease was assessed based on mortality, as well as on the appearance of hair coat ruffling, irregular movements, pelvic limb paralysis, and generalized weakness.

Histopathological analysis was carried out as follows. Lung samples were obtained on day 49, fixed in 10% (vv) neutral buffered formalin, and tissue was sectioned and stained using routine histological techniques. Hematoxylin- and eosin-stained lung sections were coded, and lesions were scored in a blinded fashion without knowledge of treatment groups. Pneumonia lesions were scored using the following system: 0=none; 1=mild; 2=moderate; 3=marked; 4=severe.

Results

Mice vaccinated with a formulation comprising tachyzoites from the NCTS8 strain of *N. caninum* and an adjuvant had a significantly lower incidence of mild pneumonia (33%) after challenge with the NC-1 strain of *N. caninum* than control mice vaccinated only with HBSS (56%) ($P<0.01$). None of the NCTS-8 vaccinated, non-challenged mice showed any sign of encephalitic disease or parasites when examined 9 weeks post-vaccination (data not shown), confirming that administration of NCTS-8 does not produce clinical disease.

The results indicate that a formulation comprising attenuated, live *Neospora* tachyzoites and an adjuvant is at least as effective and safe for use as a vaccine against neosporosis as the same formulation without an adjuvant (Table 17).

TABLE 17

Histopathological analysis of mouse lung tissue after administration of vaccine, with or without adjuvant, and challenge with the NC-1 strain of *N. caninum*.

| Treatment | Treatment Group No. | No. Mice with Lung Lesions/No. Mice Examined |
|---|---|---|
| Control Mice (vaccinated with HBSS only) | 38 | 3/5 |
| | 40 | 3/4 |
| | 42 | 2/4 |
| | 44 | 2/5 |
| Mice vaccinated with NCTS-8 without adjuvant | 39 | 0/4 |
| Mice vaccinated with NCTS-8 with adjuvant | 41 | 1/4 |
| | 43 | 0/4 |
| | 45 | 3/4 |

EXAMPLE 7

Protection of Pygmy Goats from Neosporosis

The objective of this study was to determine if vaccination of pygmy goats with an attenuated live strain of *N. caninum* can protect goats against neosporosis. More specifically, the ability of a vaccine comprising live tachyzoites of the NCTS-8 strain of *N. caninum* to protect pygmy goat does against *Neospora*-induced abortion was tested.

Materials and Methods

Pygmy goat does of approximate age range 2–5 years were randomly assigned to groups A-E (Table 18). The dose in each non-sham vaccine administration (groups A–C) consisted of $4\times10^6$ tachyzoites of the indicated strain. Following subcutaneous vaccination (1.0 ml/dose) on day 0 (primary) and day 21 (booster), the does were synchronized using LUTALYSE™ prostaglandin preparation (Upjohn-Pharmacia) (10 mg/goat, intramuscular route) on days 28 and 39. The does were bred by natural service between days 52 and 56. Pregnant does were determined by ultrasound and were between 41 and 55 days gestation at the time of challenge.

Does in groups A–D were challenged with $4\times10^6$ tachyzoites of-the NC-1 strain of *N. caninum* in serum-free maintenance medium (0.45 ml) administered by jugular i.v. The does were then monitored by ultrasound, by temperature taken daily for 7 days post-challenge, and by visual observation twice daily, and were bled once per week post-challenge.

TABLE 18

Treatment groups of pregnant pygmy goat does.

| Group | No. Does | Vaccine Strain | Adjuvant | Challenge Strain |
|---|---|---|---|---|
| A | 4 | NC-1 | None | NC-1 |
| B | 5 | NCTS-8 | None | NC-1 |
| C | 4 | NCTS-8 | Emulsion 2[a] | NC-1 |
| D | 6 | Sham | Emulsion 2 | NC-1 |
| E | 2 | Sham | None | None |

Results

All goats vaccinated with either the live NC-1 strain of *N. caninum* (group A) or the live, attenuated NCTS8 strain of *N. caninum* (groups B, C) seroconverted and had measurable IFAT titers 10 days post-booster (Table 19). These data demonstrate that NC-1 and NCTS-8 are immunogenic in pregnant goats. The GMT for group A was numerically higher than for groups B and C, suggesting enhanced replication in th host of the NC-1 strain compared to the attenuated NCTS-8 strain.

Table 20 demonstrates the ability of a vaccine comprising live, attenuated tachyzoites of *Neospora* to protect pygmy goat does against *Neospora*-induced abortion. All 4 goat does vaccinated with the live NC-1 strain (A) experienced abortion after challenge with NC-1 (0% protection). Five of 6 goat does that were sham-vaccinated (D) experienced abortion after challenge with NC-1 (17% protection). By contrast, only 2 out of 5 goat does vaccinated with NCTS-8 (B) aborted after challenge with NC-1 (60% protection), and only 2 out of 4 goat does vaccinated with NCTS-8 with adjuvant (C) aborted after challenge with NC-1 (50% protection).

These results demonstrate that pregnant pygmy goat does are substantially protected against *Neospora*-induced abortion by vaccination with live, attenuated tachyzoites of the NCTS8 strain of *N. caninum*. This is the first demonstration of the protection of a pregnant mammal against *Neospora*-induced abortion by vaccination with live, attenuated tachyzoites derived from a pathogenic strain of *Neospora*.

TABLE 19

Geometric mean reciprocal antibody titers (GMT) of pygmy goats 10 days post-booster.

| Group | Reciprocal Antibody Titer (GMT) | Range |
|---|---|---|
| A | 566 | 200–6,400 |
| B | 283 | 100–800 |
| C | 259 | 100–400 |
| D | <50 | <50 |
| E | <50 | <50 |

TABLE 20

Protection provided by attenuated live vaccine against fetal abortion induced by *N. caninum* in pygmy goats.

| Group | Vaccine | No. Aborted/ No. challenged | Percent Protection |
|---|---|---|---|
| A | NC-1 | 4/4 | 0 |
| B | NCTS-8 | 2/5 | 60 |
| C | NCTS-8 w/adjuvant | 2/4 | 50 |
| D | Sham | 5/6 | 17 |
| E | pregnancy control | not challenged | n.a. |

Deposit of Biological Materials

The following biological materials were deposited with the American Type Culture Collection (ATCC) at 12301 Parklawn Drive, Rockville, Md. 20852, USA, on Nov. 6, 1996, and were assigned the following accession numbers:

1. NC-1 strain of *Neospora caninum* in MARC145 monkey kidney cells, ATCC Accession No. CRL-12231.

2. NCTS8 strain of *N. caninum* in MARC145 monkey kidney cells, ATCC Accession No. CRL-12230.

All patents, patent applications, and publications cited above are incorporated herein by reference in their entirety.

The present invention is not limited in scope by the specific embodiments described, which are intended as single illustrations of individual aspects of the invention. Functionally equivalent compositions and methods are within the scope of the invention. Indeed, various modifications of the invention, in addition to those shown and described herein, will become apparent to those skilled in the field of microbiology, parasitology, immunology, molecular biology, veterinary medicine and related fields from the foregoing description. Such modifications are intended to fall within the scope of the appended claims.

We claim:

1. A culture of cells of an isolated strain derived from a pathogenic parent strain of a species of *Neospora*, wherein said cells exhibit attenuated pathogenicity compared to those of the parent strain, and said cells are temperature-sensitive and exhibit a reduced growth rate at the body temperature of said mammal compared to a temperature lower than the body temperature of said mammal, and wherein said cells are capable of triggering an immune response that protects a mammal against neosporosis when administered as a live vaccine.

2. The culture of claim 1, wherein the species of the parent strain is *N. caninum.*

3. The culture of claim 2, wherein the parent strain of *N. caninum* is NC-1 which is present in MARC145 monkey kidney cells having ATCC accession No. CRL12231.

4. A vaccine to protect for protecting a mammal against neosporosis, comprising a veterinarily acceptable carrier and an immunologically effective amount of live cells of an isolated strain derived from a pathogenic parent strain of a species of *Neospora*, which wherein said cells exhibit attenuated pathogenicity compared to those of the parent strain, and said cells are temperature-sensitive and exhibit a reduced growth rate at the body temperature of said mammal compared to a temperature lower than the body temperature of said mammal, and wherein said cells but which are capable of triggering an immune response that protects the mammal against neosporosis when administered as a live vaccine, and a veterinarily acceptable carrier.

5. The vaccine of claim 4, wherein the species of the parent strain is *N. caninum.*

6. The vaccine of claim 5, wherein the parent strain of *N. caninum* is NC-1 which is present in MARC145 monkey kidney cells having ATCC accession No. CRL12231.

7. The vaccine of claim 4, further comprising an adjuvant.

8. The vaccine of claim 7, wherein the adjuvant is an oil-in-water emulsion.

9. A method for preparing a culture of attenuated cells of a species of *Neospora* for use in a vaccine that protects a mammal against neosporosis, comprising modifying cells from a pathogenic parent strain of a species of *Neospora*; selecting and clonally propagating one or more modified cells that exhibit attenuated pathogenicity compared to cells of the parent strain, and that are temperature-sensitive and exhibit a reduced growth rate at the body temperature of said mammal compared to a temperature lower than the body temperature of said mammal; and selecting and clonally propagating one or more attenuated cells which are capable of triggering an immune response that protects the mammal against neosporosis when administered in a live vaccine.

10. The method of claim 9, wherein the species of the parent strain is *N. caninum.*

11. The method of claim 10, wherein the parent strain of *N. caninum* is NC-1 which is present in MARC145 monkey kidney cells having ATCC accession No. CRL-12231.

12. A method for preparing a vaccine to protect a mammal against neosporosis, comprising modifying cells from a pathogenic parent strain of a species of *Neospora*; selecting and clonally propagating those modified cells that exhibit attenuated pathogenicity compared to cells of the parent strain, that are temperature-sensitive and exhibit a reduced growth rate at the body temperature of said mammal compared to a temperature lower than the body temperature of said mammal, and that are capable of triggering an immune response an the mammal that protects against neosporosis when administered in a live vaccine; and combining an immunologically effective amount of the attenuated cells with a veterinarily acceptable carrier in a form suitable for administration as a live vaccine to the mammal.

13. The method of claim 12, wherein the species of the parent strain is *N. caninum.*

14. The method of claim 13, wherein the parent strain of *N. caninum is NC*-1 which is present in MARC145 monkey kidney cells having ATCC accession No. CRL-12231.

15. The method of claim 14, wherein the strain of attenuated cells is NCTS-8 which is present in MARC145 monkey kidney cells having ATCC accession No. CRL-12230.

16. The method of claim 12, further comprising adding an adjuvant to the vaccine.

17. The method of claim 16, wherein the adjuvant is an oil-in-water emulsion.

18. A method of vaccinating a mammal against neosporosis, comprising administering to the mammal an immunologically effective amount of a vaccine and a veterinarily acceptable carrier, wherein said vaccine comprises live cells of an isolated strain derived from a pathogenic parent strain of a species of *Neospora*, wherein said cells exhibit attenuated pathogenicity compared to those of the parent strain, and said cells are temperature-sensitive and exhibit a reduced growth rate at the body temperature of said mammal compared to a temperature lower than the body temperature of said mammal, and wherein said cells are capable of triggering an immune response that protects the mammal against neosporosis.

19. The method of claim 18, wherein the species of the parent strain is *N. caninum.*

20. The method of claim 19, wherein the parent strain of *N. caninum is NC*-1 which is present in MARC145 monkey kidney cells having ATCC accession No. CRL-12231.

21. The method of claim 20, wherein the strain of attenuated cells is NCTS-8 which is present in MARC145 monkey kidney cells having ATCC accession No. CRL-12230.

22. The method of claim 18, wherein the vaccine further comprises an adjuvant.

23. The method of claim 22, wherein the adjuvant is an oil-in-water emulsion.

24. The method of claim 18, wherein the mammal is selected from the group consisting of dogs, cows, goats, sheep and horses.

25. A combination vaccine, comprising an immunologically effective amount of live cells of an isolated strain derived from a pathogenic parent strain of a species of *Neospora*, wherein said cells exhibit attenuated pathogenicity compared to those of the parent strain, and said cells are temperature-sensitive and exhibit a reduced growth rate at the body temperature of said mammal compared to a temperature lower than the body temperature of said mammal, and wherein said cells are capable of triggering an immune response that protects the mammal against neosporosis when administered as a live vaccine together with one or more antigens other than a *Neospora* antigen that trigger an immune response that protects the mammal against a disease or a pathological condition, and a veterinarily acceptable carrier.

* * * * *